US006962573B1

(12) United States Patent
Wilcox

(10) Patent No.: US 6,962,573 B1
(45) Date of Patent: Nov. 8, 2005

(54) C-SHAPED CROSS SECTION TUBULAR OPHTHALMIC IMPLANT FOR REDUCTION OF INTRAOCULAR PRESSURE IN GLAUCOMATOUS EYES AND METHOD OF USE

(76) Inventor: Michael J. Wilcox, 6555 Delmonico Dr., Apt 212, Colorado Springs, CO (US) 80919

( * ) Notice: Subject to any disclaimer, the term of this patent is extended or adjusted under 35 U.S.C. 154(b) by 284 days.

(21) Appl. No.: 09/691,671

(22) Filed: Oct. 18, 2000

(51) Int. Cl.[7] .............................................. A61M 5/00
(52) U.S. Cl. .......................................... 604/9; 606/108
(58) Field of Search ............................... 604/294, 264, 604/8–10, 20–30, 160–161, 164, 289, 540; 606/1, 4, 6, 108, 166, 184–185; 623/4.1, 623/5.11

(56) References Cited

U.S. PATENT DOCUMENTS

| | | | |
|---|---|---|---|
| 3,796,370 A | * | 3/1974 | Speers et al. ............ 229/103.1 |
| 4,883,468 A | * | 11/1989 | Kousai et al. .............. 604/161 |
| 5,195,978 A | * | 3/1993 | Schiffer ....................... 604/161 |
| 5,395,335 A | * | 3/1995 | Jang ....................... 604/102.02 |
| 5,800,414 A | * | 9/1998 | Cazal .......................... 604/264 |
| 6,471,666 B1 | * | 10/2002 | Odrich ........................... 604/8 |

* cited by examiner

Primary Examiner—Nicholas D. Lucchesi
Assistant Examiner—Michael M Thompson
(74) Attorney, Agent, or Firm—Richard W. Hanes; Hanes & Schutz, P.C.

(57) ABSTRACT

A tube for implantation into the eye for replacement conduction of aqueous humor from the chambers of the eyeball to the subconjunctival tissue and ultimately to the venous system is comprised of an elongated fluid conducting conduit having distal and proximate ends, a sidewall and an interior passageway and at least one longitudinally extending opening in the sidewall that exposes the interior passageway and at least one nidi-forming structure carried by the conduit and extending laterally therefrom to implement the formation of at least one aqueous filtration bleb in the tissue of the eyeball. In one embodiment, the tube also contains at least one releasable ligature circumscribing the conduit. In another embodiment, the tube also contains an anchor appended to the conduit to prevent it from migrating from its placement site.

7 Claims, 4 Drawing Sheets

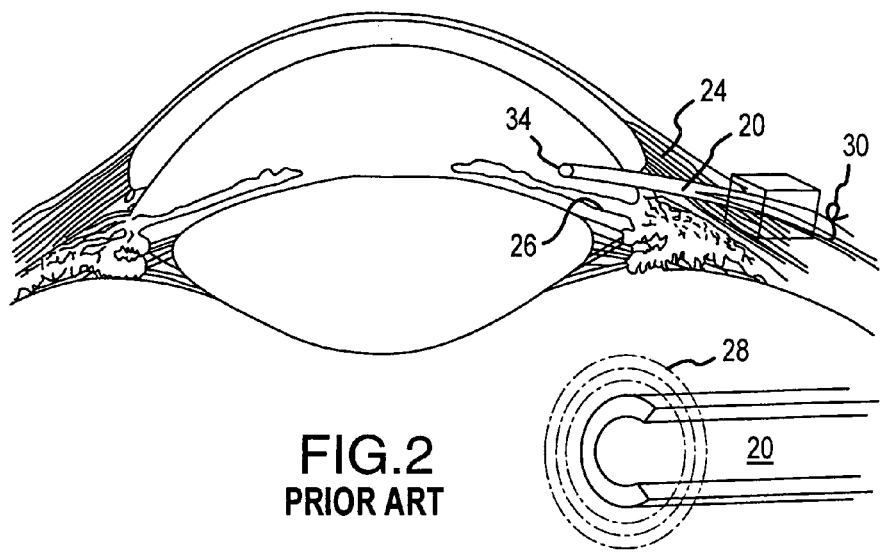
FIG.2
PRIOR ART
FIG.1
PRIOR ART
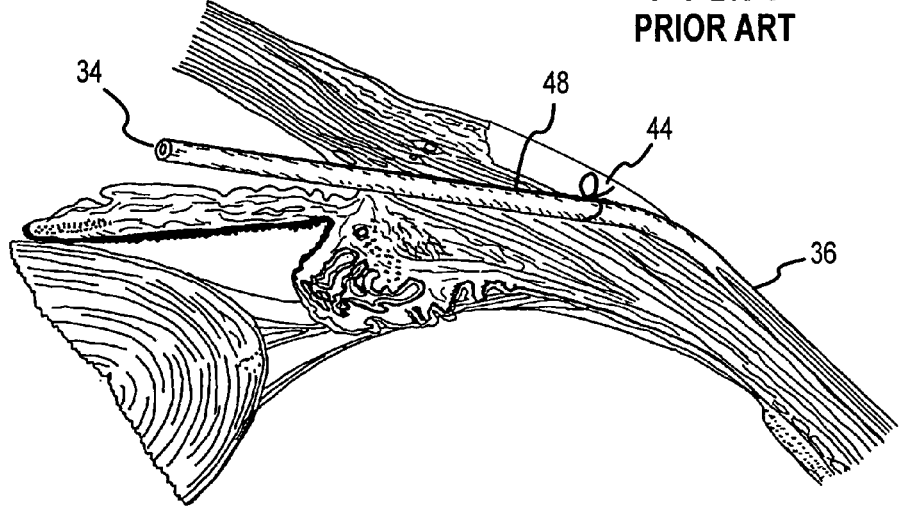
FIG.3

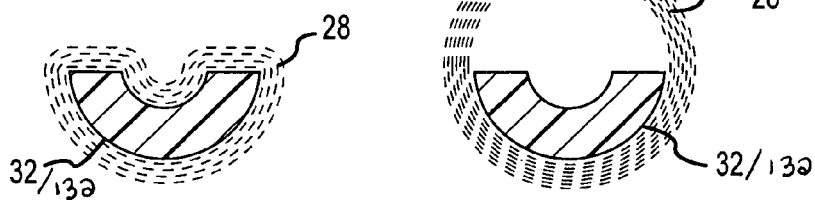
FIG.10   FIG.11
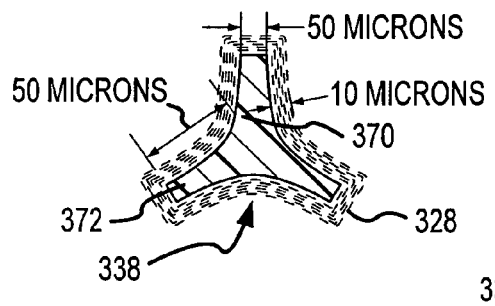 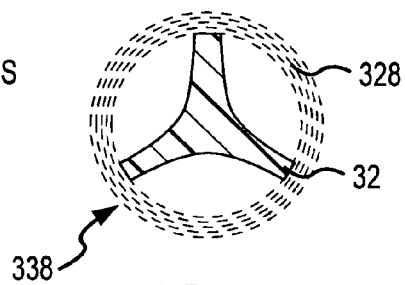
FIG.13   FIG.14
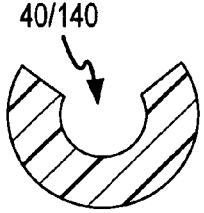 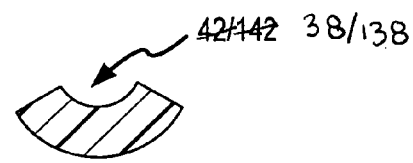
FIG.15   FIG.16
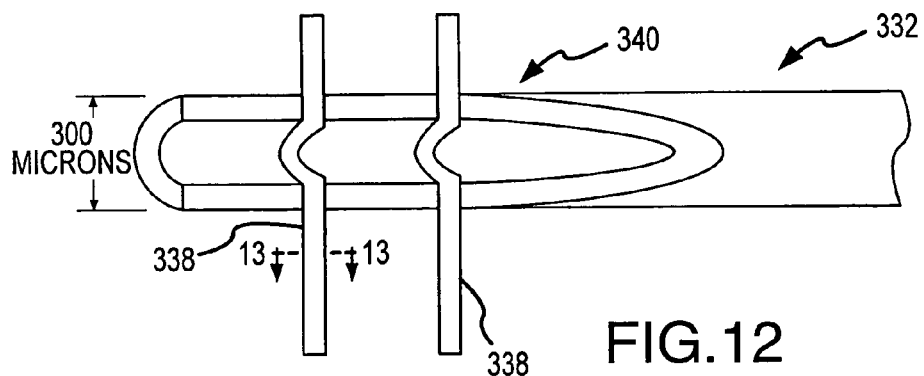
FIG.12

C-SHAPED CROSS SECTION TUBULAR OPHTHALMIC IMPLANT FOR REDUCTION OF INTRAOCULAR PRESSURE IN GLAUCOMATOUS EYES AND METHOD OF USE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to tubular shunts for the control of intraocular pressure in glaucomatous eyes, and more specifically to a tubular shunt with a C-shaped radial cross section along portions of the tube and a method of controlling intraocular pressure.

Glaucoma is a disease characterized by high pressure inside the eye, leading to the loss of retinal nerve fibers with a corresponding loss of vision. Glaucoma therefore is a disease affecting the optic nerve, the nerve bundle which carries visual information to the brain.

The eyeball is basically a rigid sphere filled with fluid. Positive pressure inside the eye is needed to keep the retina attached to the back of the eye. Pressure is maintained by fluid production from a bilayer of cells on top of the ciliary body, which is located adjacent to the iris root in the eye. This clear fluid called aqueous humor carries nutrients to the lens and cornea of the eye, both of which have no blood supply. The shape of the front part of the eye is maintained by aqueous humor production. The ciliary body is located behind the colored part of the eye (iris). Fibrous strands called zonule fibers attached to the ciliary body support the lens. Tension from the rigid structure of the eye, transferred to these zonules, deforms the lens and focuses the image onto the retina. Radial muscles behind the ciliary body, contract and release tension on the zonules allowing the lens to round up and focus near images onto the retina. Aqueous humor flows into the front of the eye through the pupil and drains out of the eye through the trabecular meshwork. The trabecular meshwork is a spongy mass of tiny channels located in the drainage angle, between the clear covering of the eye (cornea) and the colored part (iris) at the location where the iris meets the white outer covering of the eye (sclera). The fluid drains from the meshwork into a small canal, called Schlemm's canal, which is connected to the bloodstream at the venous return from the eye. Aqueous humor is produced by the ciliary body and removed from the eye at a constant rate (about 1.0 tsp or 5.0 ml per day) to maintain a constant pressure in the front (anterior) chamber of the eye. While pressure in the eye varies throughout the day, the average pressure within the eye is 10 mm Hg to 21 mm Hg. If the resistance to fluid flow increases or the amount of fluid generated exceeds the capacity of the meshwork to vent it, pressure inside the eye increases, similar to over-inflating a tire. The higher the pressure inside the eye, the greater the chance of damage to the optic nerve. Glaucoma is the leading cause of blindness in third world countries, and the leading cause of preventable blindness in industrial countries. It affects approximately 2% of the entire population; blacks and native Americans are disproportionately represented, with elevated occurrence of the disease. Early signs of the disease are often observed as enlargement and cupping of the physiological blind spot which is the point where the optic nerve leaves the eyeball and projects to the brain. Blind spots in the superior and inferior visual fields (called arcuate scotomas) correspond to the loss of nerve cells. In later stages more visual field losses eventually end in total blindness. If the drainage angle becomes blocked, fluid pressure transferred throughout the eye increases, damaging the optic nerve—the part of the eye responsible for transforming images into impulses the brain can translate. This damage results in partial or complete blindness.

In acute angle-closure glaucoma, eye pressure builds up rapidly. This type of glaucoma commonly occurs in individuals who have narrow anterior chamber angles. In these cases, aqueous fluid behind the iris cannot pass through the pupil and pushes the iris forward, preventing aqueous drainage through the angle. It is as though a sheet of paper floating near a drain suddenly drops over the opening and blocks the flow out of the sink. In cases of acute angle closure glaucoma, one may experience blurred vision, halos around lights, pain, nausea, and vomiting. If pressure within the eye is not immediately relieved, blindness may result in a matter of days. Migration of pigmented epithelial cells in the eye either congenital or following blunt trauma can occlude angle structures quickly elevating pressure in the eye. Primary open-angle glaucoma has a longer time course and many components that exacerbate the condition. The end effect is the same. Secondary glaucoma can occur from inflammation, degeneration, trauma, or tumor growth within the eye. Certain medications are also reported to cause secondary glaucoma. In summary, the disease glaucoma is a plethora of conditions that elevate intraocular pressure. Left uncontrolled, high intraocular pressure leads to blindness.

In the detection of glaucoma, measuring the pressure in the eye by itself does not give a diagnosis of glaucoma. Of more importance is the direct observation of damage to the optic nerve itself and sometimes the nerve fiber layer of the retina. Quantifying a loss of vision in part of the visual field consistent with observed nerve fiber loss is the true definitive diagnosis for glaucoma. Loss of nerve fibers caused by glaucoma cannot be reversed. Therefore, the goal in the management of glaucoma is to reduce the intraocular pressure to the point whereby the remaining healthy nerve fibers are able to maintain function.

Glaucoma is usually controlled with eye drops taken several times a day, sometimes in combination with pills. These medications are used to prevent damage to the optic nerve by decreasing eye pressure, either by slowing the production of aqueous fluid within the eye or by improving the flow leaving the drainage angle structures. If topical and/or oral therapy does not control intraocular pressure, laser surgery may be an effective alternative treatment or adjunct. A laser can be used in one of two ways. In open-angle glaucoma, the laser is used to puncture a hole and enlarge the drain (laser trabeculectomy) or a low power beam can be used to form scar tissue that contracts and pulls on the meshwork (trabeculoplasty) to improve outflow of aqueous humor and lower pressure in the eye. In angle-closure glaucoma, a laser can create a hole in the iris (iridotomy) to improve the flow of aqueous fluid to the drain. Another surgical procedure using a knife controls pressure by creating a new drainage channel, trabeculectomy, through the angle structures to the extracellular space beneath the conjunctiva. If the hole through the meshwork is too large, the outflow rate will exceed production, reducing the intraocular pressure so low (a condition called pthisis bulbi) that the retina is in danger of detachment. Once the anterior chamber is breached, a capsule often forms around a fluid filled cavity called a bleb, a medical term for a blister, and vents aqueous humor from the eye, thereby lowering the intraocular pressure. The capsule prevents decompression of the anterior chamber by providing resistance to flow. The capsule filters aqueous humor to the extracellular space under the conjunctiva.

Scarring of the opening after surgery is the most common problem with trabeculectomy. Likewise, the capsule can scar with fibrous tissue and cease filtration. The risk of excessive scarring is sometimes decreased when corticosteroids are used after surgery. An antifibrotic, 5-fluorouracil, may be used to prevent scarring, which is the most common cause of bleb failure. If bleb failure continues to be a problem, a drainage device called a seton may be placed in the eye to help keep the channel open and draining fluid.

Earlier work by the inventor, described in Michael J. Wilcox, Ph.D., and Donald S. Minckler, M.D., "Hypothesis for Improving Accessory Filtration by Using Geometry," *Journal of Glaucoma* 3:244–247 (1994), proposes an improved tube shunt which should allow control of intraocular pressure in glaucomatous eyes that do not respond to other approaches. That hypothesis was recently tested and the performance of the device reported in *Journal of Glaucoma* 9:74–82 (2000). The overwhelming cause of compromise in accessory filtration devices is excessive fibrosis, i.e., buildup of scar tissue, on the filtering capsule over time. In conventional implants, inserting a tube provides a conduit for aqueous humor to bypass angle structures and enter the large blister-like cavity called a bleb, which is formed around a plate to provide a two dimensional nidus of a given surface area. The fibrous capsule formed around the cavity provides most of the resistance to outflow of aqueous that filters into the adjacent extracellular space. Continuous buildup of fibrous tissue in the capsule leads to decreased outflow with consequent re-elevation of intraocular pressure and failure of the device. The *Journal of Glaucoma* (1994) article described two recent studies that may improve understanding the mechanisms of filtration and fibrosis and could supply a countermeasure to this stimulus to fibrose. First, studies of primate eyes with experimental glaucoma had demonstrated that aqueous outflow through a Molteno implant functions by passive filtration, with little contribution from vascular routes. Second, recent experimental evidence suggested that mechanical deformation of cultured fibroblasts stimulates them to lay down more extracellular matrix. Based on these two premises, a design was conceived for countering this stimulus by using the geometry of the implant to reduce tension on the capsule surrounding the implant. An additional advantage of that new implant design is that it provided an easily customized total surface area that will minimize the volume of functioning blebs and, at the same time, maintain or even increase the total filtering surface of the capsule. Decreasing the size of the lumen of a bleb alone will reduce surface tension on the capsule wall, thereby reducing the fibrosing stimulus and extending the useful life of accessory filtration devices. Moreover, decreased volume will reduce extraocular muscle complications. Consistent with a passive filtration mechanism, total outflow through conventional implants is proportional to the surface area of the capsule. Each glaucomatous eye differs in the extent of damage to the normal aqueous outflow routes. Therefore, easily customized surface area allows tailoring each implant to the accessory filtration needed. In the case of the present device, the surface area is proportional to the length of the implant. Cutting appropriate lengths of tubing will give the desired filtration surface area.

Capsule fibrosis remains the major source of compromise for accessory filtration devices. It has been suggested that aqueous humor has a stimulatory effect on fibroblasts, causing them to lay down more extracellular matrix and effectively doom these filtering procedures. However, improved filtration in mature, functioning blebs suggests that perfusion with aqueous humor paradoxically contributes to improved permeability. This notion is consistent with the idea that capsules do become better filters with time, provided intraocular pressure remains controlled. In time, the quality of the capsule changes and the bleb acquires a more diffuse boundary. From his original studies, Molteno noted poor long-term control of intraocular pressure if excessive postoperative inflammation remained, resulting in immediate re-elevation of intraocular pressure. Alternatively, if intraocular pressure were well controlled after tube opening and inflammation were minimal, long periods with controlled intraocular pressure followed. Molteno has justified his initial use of systemic antifibrosis therapy on the basis of suppressing inflammatory response, to minimize postoperative capsular fibrosis. Indeed, his series of long-term successes with histological study (some exceeding 15 years) show minimal capsule fibrosis and virtually nonexistent inflammatory infiltrate.

Retrospective examination of these observations suggested that increased tension on the capsule due to high pressure stimulated fibrosis. Hypervascularity of a bleb is associated with poor function, presumably due to fibrosis. In other tissues, inflammatory infiltrates bring enzymes that initially degrade collagen, but this episode is followed by remodeling and augmented rebuilding of the collagen matrix. Research into vascular mechanisms of fibrosis offered insight into the reason for this extracellular buildup. Mechanical tension induces connective tissue synthesis by stimulating cells to produce more extracellular matrix. Mechanically stretching cultured mesangial cells increases their production of collagen and other extracellular matrix components, without affecting cell division. Once matrix deformation ends, cells return to a more quiescent state, suggesting that vascular leakage continues to stretch the matrix and stimulates fibroblasts to reinforce it.

Collagen deposition in a fibrosing matrix is an extracellular process. In aqueous humor there are usually no inflammatory infiltrates to stimulate fibroblasts. Therefore, if inflammation of the bleb can be kept to a minimum, fibrosis will be minimized. However, aqueous outflow can function to wash out molecular collagen before it incorporates into the extracellular matrix. Hence, two processes must be interacting in functional blebs and regulating both is required to minimize fibrosis. First, tension stimulates fibroblasts to excrete more pro-collagen, which becomes incorporated into the extracellular matrix. Second, aqueous perfusion washes out pro-collagen before it becomes part of the matrix. Therefore, two approaches may limit the incessant collagen deposition: decreased pro-collagen production by reducing surface tension and/or increased outflow to wash out molecular collagen before incorporation into the extracellular matrix.

In the case of long-term failures in accessory filtration, fibroblasts apparently proliferate or migrate into a stretched capsule and lay down matrix in an attempt to strengthen the relatively thin walled structure. A fibrous extracellular matrix compromises filtration, leading to decreased outflow and re-elevation of intraocular pressure. The role of surface tension in capsule structure and function has both a mechanical and a geometrical component to it. In Laplace's well-known soap bubble experiment, he showed that a large pressurized cavity exerts greater tension on its wall than a small cavity does at the same internal pressure. Laplace's law states that along a single dimension, tension on the wall is proportional to the pressure and also to the radius of the cavity. The same concept has been used to explain the difference in thickness between large vessels and capillaries. Even though the pressure gradient across a capillary is much higher than the gradient across the vena cava, the thin walls of capillaries do not rupture because the tension on their walls is actually less than tension on the wall of the vena cava. This is due simply to the smaller diameter of the lumen of the capillary.

Conventional implant devices for reduction of intraocular pressure are exemplified in the patents to Molteno (U.S. Pat. No. 4,750,901), Schocket (U.S. Pat. No. 4,826,478), Mateen (U.S. Pat. No. 5,785,674), and Baerveldt (U.S. Pat. No. 6,050,970). These conventional implant devices all have a tube extending from the anterior chamber to some sort of plate-or loop of predetermined size and shape, around which forms a filtration capsule. The filtration capacity of a capsule formed in this manner is therefore predetermined by the total surface area of the plates or loops around which the capsule forms as well as the permeability of the capsule as determined by its thickness. This includes an anterior chamber tubule shunt to an encircling band and an anterior chamber shunt to a surgical membrane. These are installed far behind far behind the extraoccular muscles around the equator of the eyeball, in order to avoid muscle complications. Still these other devices have problems with excess fibrosis. My present invention is the only one that uses the approach of minimizing the dimension of the lumen in order to minimize fibrosis. I have achieved this in animal studies and my present research suggests that the amount of fibrosis can be controlled with the present invention thereby producing a functional implant with a lifetime equal to that of the person receiving the implant.

Reducing tension on the formed capsule wall by decreasing the size of the lumen was a logical design modification. A cylinder is an ideal geometry for minimizing volume, while maximizing surface area. The small diameter of the cylindrical bleb decreases tension on the formed capsule wall and, thus, decreases fibrosing stimuli. The prior art implant shown in FIG. 2 is a simple, small-diameter tube 20 with a C-shaped cross section shown in FIG. 1 and variable length. The device has no large separate explant around which a capsule would form and no large distended space filled with aqueous. The entire side is open so that aqueous has access to the filtering surface. There are no slits, holes, or valves to occlude. The proximal portion 34 of the tubal implant is inserted through the limbal tissues 24 and positioned just above the iris root 26. The distal portion 36 of the tube is opened along its length to prevent tissue occlusion of the tube inside the small-caliber, cylindrical bleb. The portion of the implant and its bleb outlined by a cube in FIG. 2 is shown enlarged in FIG. 3. Once a proper capsule has formed around the implant and the ligature 30 has been released, pressure from aqueous humor in the anterior chamber lifts the capsule from the open side of the latex tubing and forms a cylindrical bleb 28, depicted in FIG. 1 as a diffuse sheath surrounding a latex implant. Only a portion of the implant is depicted. The implant, in fact, folds back on itself to fill a pocket excavated under the conjunctiva.

As with most surgical intervention, in the early postoperative days, there is a seton effect, where aqueous leakage occurs along the path where the implant enters the anterior chamber. It is during this period that the eye is at risk due to hypotony, i.e. low pressure. Therefore, like the Molteno implant, the newly installed tube is ligated initially, until a proper capsule can grow around the implant. The weakest tissue adhesion point in implants is between the fibrous capsule and the latex tubing. The portion removed along the side of the implant to form a C-shaped cross section as shown in FIG. 2 ensures that once the ligature 30 is released, pressurized aqueous will lift the capsule away from the latex tubing and form a cylindrical bleb. The latex remains free-floating within the bleb to prevent constriction, collapse, or adhesions forming inside the bleb. Once a capsule is inflated, a tube 85 mm long and 0.3 mm in diameter would produce a cylindrical bleb 1 mm in diameter, providing a surface area equivalent to a single 13 mm-diameter Molteno plate. The tubing folds back on itself and occupies even less scleral surface than a Molteno implant, yet provides an even larger filtering surface and, consequently, larger outflow capacity in the same space. The total surface area is linearly proportional to the length of the tube installed and this can be easily controlled by adjusting tube length at the time of installation.

A cylinder provides an ideal geometry for both these qualities. The additional benefit of customized surface area and minimal volume had other desirable effects that avoid complications seen with the use of other implant designs. This concept was tested in animals and recently reported in *Journal of Glaucoma* 9; 74–82 (2000). An improved outflow from this accessory filtration device was attained by reducing surface tension on the capsule and increasing the effective surface area filtering aqueous, attaining an eight-fold increased hydraulic conductivity of the capsule with a concomitant reduction in capsule thickness compared to Baerveldt and Molteno implants. Reduced tension on the bleb counters the stimulus for capsular fibrosis and should extend the useful lives of these accessory filtration devices.

Further improvements, however, may still be made to the earlier improved tube shunt apparatus and procedure.

It is, therefore, a principal object of the present invention to provide a post-surgical ability to customize the implant by increasing its surface area, without the need of further surgery or an additional implant, by simply removing a ligature or series of ligatures after post-surgical intraocular pressure has been determined. This results in increased flow of aqueous humor and reduced intraocular pressure.

Another object of the present invention is to provide an anchor for the implant, which is attachable to the sclera at the limbus. This has the advantage of preventing migration of the implant into the anterior chamber.

Another object of the present invention is to provide a further three-fold reduction in bleb diameter resulting in a capsule only one cell layer thick, with the advantage that the resultant structure approaches the dimensions of the trabecular meshwork in a human eye.

Another object of the present invention is to provide a post-surgical ability to customize the total surface area of the implant by increasing filtration surface area without the need of further surgery or an additional implant by simply removing, after post-surgical intraocular pressure has been determined, a ligature or series of ligatures located at intact portions along the length of the insert situated between C-shaped, open, cross-sectional portions.

Another object of the present invention is to provide an implant with a resultant reduced surface tension on the wall of the implant with the advantage that fibrosis is minimized, thereby allowing continuous and on-going hydraulic conductivity of aqueous with a concomitant reduction in intraocular pressure to a safe and stabilized level.

Another object of the present invention is to provide an implant nidus with a scalloped cross-section whereby separation of the fibrous tissue of the bleb from the implant nidus is facilitated and the cross-sectional dimension of the nidus may be reduced as compared to a smooth, round surface.

Another object of the present invention is to provide a method for reducing intraocular pressure by creating a cylindrical bleb for producing improved accessory filtration by implanting a cylindrical tube having a proximal end and distal end, the distal portion of the cylindrical tube side wall being removed, into an eye to serve as a nidus for a conduit of aqueous humor to bypass angle structures.

These and other objects, features and advantages of the present invention will be apparent in the description of representative embodiments.

SUMMARY OF THE INVENTION

The present invention comprises an implant for the reduction of intraocular pressure. The novelty of the present invention is a post-surgical ability to customize the total surface area of the implant, increasing fluid filtration by increasing surface area without the need of further surgery or an additional implant. After post-surgical intraocular pressure has been determined, a ligature or series of ligatures located at intact portions along the length of the implant situated between C-shaped, open, cross-sectional portions can simply be removed. The present invention also comprises an implant anchor attachable to the sclera at the limbus and having the advantage of preventing migration of the implant into the anterior chamber. The invention provides a further three-fold reduction in bleb diameter as compared to the prior art resulting in a thinner capsule with hydraulic conductivity higher than capsules around implants of any prior art. Such a capsule, in the best case only one cell layer thick, has the further advantage that the resultant structure approaches the dimensions of the normal trabecular meshwork in a human eye. The small diameter of the present invention provides an implant with a resultant low surface tension on the wall of the capsule with the advantage that fibrosis is minimized, thereby allowing a constant filtration rate of aqueous and reduction in intraocular pressure to a safe and stabilized level.

The implant consists of a cylindrical tube with a diameter of approximately three hundred micrometers and with proximal end and a distal end for implantation into an eye to serve as a conduit for aqueous humor to bypass angle structures. Where a lateral portion of the tube is removed, the interior of the tube is exposed creating an open side walled portion of the tube. A cross section of the open side walled portion normal to the length of the tube is in the shape of an arch. The tube may further comprise a series of lateral portions where the sidewall of the tube is removed. Removed lateral portions are located serially along the length of the tube and separated by whole cylindrical portions. Lateral portions are situated in a non-overlapping configuration. A ligature is tied to each of the whole cylindrical portions whereby flow through the whole cylindrical portions is prevented until the ligature is released. A second form of anchor comprises a split end of the tube wherein the end of the tube is split multiple times.

The invention may also incorporate a portion, scalloped (or asterisk-shaped) in cross section, extending outwardly from at least one side of the exposed interior of the tube to further serve as a nidus for cell growth and capsule formation. The scalloped portion has a radius of 50 microns from the center to the tip of the scallop, a tip width of 5 microns, and preferably extends between 10 millimeters and 20 millimeters in a normal direction from the tube. If the capsule or bleb is deposited onto a smooth, solid surface, pressure from the anterior chamber may not always be sufficient to separate the capsule from the smooth, solid surface and inflate a volume in the subconjunctival space. If a bleb does not form or if the capsule remains attached to the implant material, it will not vent fluid and will not become functional.

The method of the present invention for reducing intraocular pressure by creating a cylindrical bleb for producing improved accessory filtration comprises the steps of implanting a cylindrical tube having a proximal end and distal end. The proximal end of the tube is intact and serves as a conduit for aqueous humor to bypass the angle structures. The distal portion of the cylindrical tube has the side wall removed to allow fibrous tissue to form on its surface. Once this fibrous capsule has formed, a ligature around the intact portion of the tube is removed. Pressurized aqueous humor from the anterior chamber elevates the capsule into a functional bleb that filters aqueous humor into the extracellular space underneath the conjunctiva. This fluid is eventually removed from the eye and reenters the vascular circulation. Installation consists of the steps of incising the conjunctiva, elevating the conjunctiva from the sclera, implanting the distal portion of the cylindrical tube under the conjunctiva, anchoring the proximal end of the cylindrical tube to the sclera at the limbus, inserting the proximal, intact end of the tube into the anterior chamber through a needle track, ligating the proximal end to prevent hypotony, allowing approximately one week for cell growth around the tube, releasing a ligature around the proximal end after approximately one week to inflate the bleb, measuring the intraocular pressure to determine if additional drainage is required, if additional drainage is required, releasing additional ligatures whereby additional blebs are inflated.

BRIEF DESCRIPTION OF THE DRAWINGS

The present invention will be more clearly understood from a reading of the following detailed description in conjunction with the accompanying drawings wherein:

FIG. 1 is a schematic representation of a prior art implant;

FIG. 2 is a schematic representation of the anterior segment of an eye with a prior art implant in place;

FIG. 3 is a cross section of the ciliary root and iris of an eye and an implant in place;

FIG. 10 is a cross section of a C-shaped distal nidus of the implant of FIGS. 4 and 5 during capsule (or bleb) formation taken alone lines 10—10;

FIG. 11 is a view similar to that of FIG. 10 but showing the inflation of the bleb following removal of the ligature;

FIG. 12 is a schematic representation of another embodiment of the invention employing scalloped nidus portions extending laterally from a cutaway portion of the implant;

FIG. 13 is a cross section of a scalloped portion of the FIG. 12 implant taken along lines 13—13 of FIG. 12 during capsule (or bleb) formation;

FIG. 14 is a view similar to that of FIG. 13 but showing the inflation of the bleb following removal of the ligature;

FIG. 15 is a cross section of the implant tube taken along lines 15—15 of FIGS. 4 and 5;

FIG. 16 is a cross section of the implant's lateral nidus projection taken along lines 16—16 of FIGS. 4 and 5.

DETAILED DESCRIPTION

Figure 4:
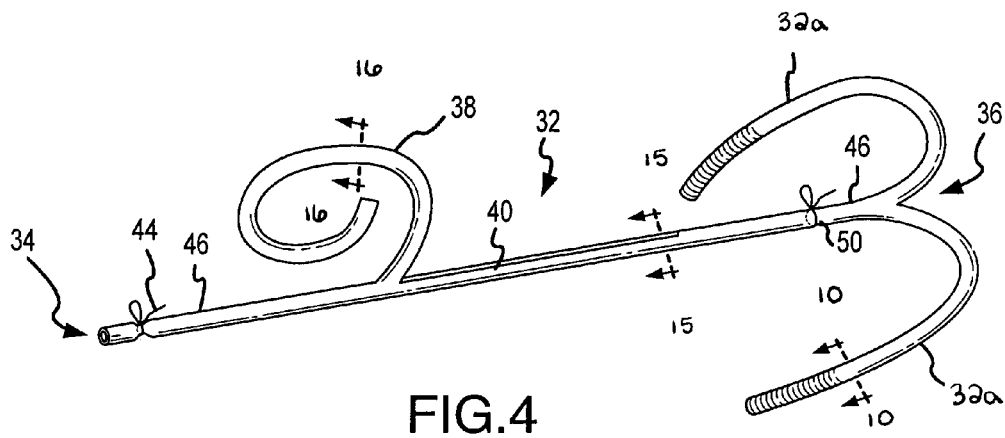
FIG. 4 is a schematic representation of a single-section, bifurcated implant.

Referring now to FIG. 4 of the drawings, there is shown a schematic representation of the ophthalmic implant, cylindrical tube 32, with the proximal end 34 shown on the left and the distal end 36 shown on the right. It is to be noted that tube 32 may be and includes tubes of a cross-sectional shape other than circular, e.g. triangular, rectangular, pentagonal, L-shaped, etc. This is because the capsule formed around the tube when the capsule is inflated will be essentially a cylindrical shape as it is inflated by fluid. In practice, the conjunctiva is incised about 3 mm from the limbus and the conjunctiva is elevated by blunt dissection 10–12 mm back so that the longer distal end of the implant can be pushed into the pocket so formed. Through this same incision, a needle track is made entering the anterior chamber just in front of the iris. The proximal end 34 is inserted through this needle track 48, shown in FIG. 3, made by a 23 gauge needle. The small gauge ensures that limbal tissues adhere to the latex tubing without leakage so that intraocular pressure from aqueous humor can reform the anterior chamber. The tube serves as a permanent conduit for passage of aqueous humor past the angle structures. The distal tubing serves as a nidus for the growth of fibrous, permeable tissue. Once elevated from the latex this fibrous tissue forms a filtration capsule that drains aqueous humor into subconjunctival tissue. Venting this fluid is controlled by the hydraulic resistance of the capsule and controls intraocular pressure preventing further damage to the optic nerve, which is the characteristic of the disease, glaucoma.

Figure 7:
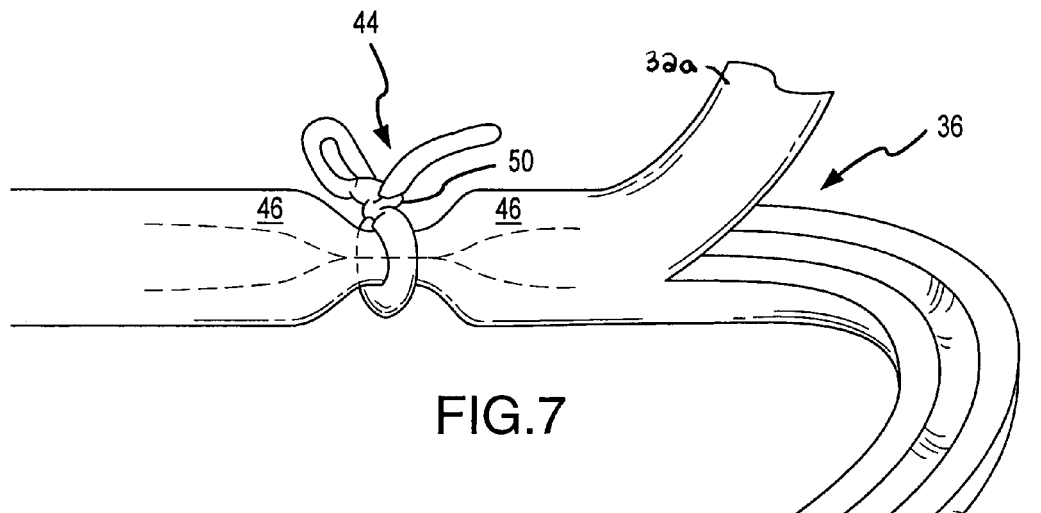
FIG. 7 is an enlarged fragmentary view of the distal end of the implant of FIGS. 4 and 5.

The inserted tube may be made of latex or any other suitable, flexible material. Flexible material is chosen to prevent erosion of eye tissues in contact with the implant. The proximal end 34 comprises a whole cylindrical portion 46 which is ligated, i.e., tied off with ligature 44 as shown in FIGS. 3 and 7. The ligatures comprise slip knots for ease of removal after insertion of the implant. It is to be noted that any equivalent to a slip knot which would allow simple opening of a closed off portion could be used. Ligature 44 also serves to anchor tube 32 to the sclera at the limbus where the tube enters the anterior chamber through the needle track 48. As with most surgical intervention, in the early postoperative days, there is a seton effect, where aqueous leakage occurs along the path 48 where the implant 32 enters the anterior chamber. It is during this period that the eye is at risk due to hypotony, i.e., low pressure and possible retinal detachment. Therefore, a newly installed tube is ligated initially, until a proper capsule can grow around the implant. A lesser desired alternative to litigating the tube is use of soluble plug surrounding the tube. The weakest tissue adhesion point in the implant 32 is between the fibrous cellular capsule and the latex tubing. The implant lateral portion 38 is peeled back (similar to peeling a banana) or otherwise removed along the open side 40 of the implant to form a nidus for fibrous cell growth along C-shaped cross sections, as shown in FIGS. 15 and 16. Once ligature 44 is released, pressurized aqueous will lift the capsule away from the latex tubing and form a bleb 28. FIG. 10 shows the fibrous capsule 28 prior to release of ligature 44 and FIG. 11 shows the fibrous capsule 28 as inflated after release of ligature 44. The latex tube remains free-floating within the bleb to prevent constriction, collapse, or adhesions forming inside the bleb. Alternatively, the distal tube 32 may be made of dissolvable material which is eventually sloughed off. The proximal portion must remain intact and permanently in place or else the tight limbal tissues will occlude the opening through the angle structures and aqueous passage will be blocked.

The tube of the present embodiment is bifurcated at distal end 36, FIG. 4. Bifurcated portions 32a and lateral portion 38 may be shaped as shown in FIGS. 10 and 16 respectively. Bifurcated portions 32a and lateral portion 38 serve as nidi for fibrous tissue growth 28 as shown in FIG. 10. After 5–7 days the capsule has had sufficient time to form with an appropriate thickness. Elevation of the capsule from the implant by pressurized aqueous forms a bleb that filters aqueous into subconjunctival tissues. Bifurcated portions 32a serve as a second anchor after a bleb is formed around these bifurcated portions. Thereafter, ligature 50 is released thereby inflating bleb 28, FIG. 11, and allowing aqueous to pass from the anterior chamber to subconjunctival tissue.

Figure 5:
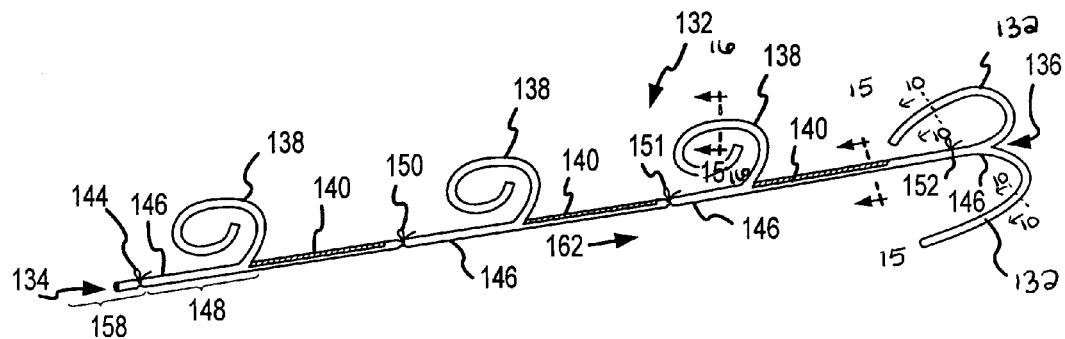
FIG. 5 is a schematic representation of multiple-section, bifurcated implant.
Figure 6:
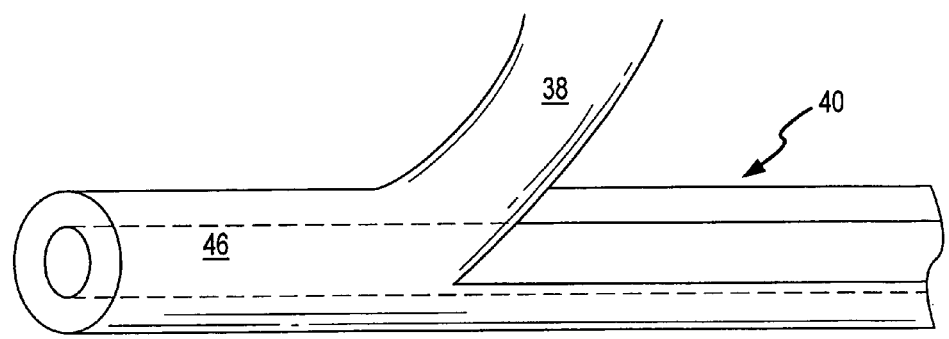
FIG. 6 is an enlarged fragmentary view of the junction between the main tubular body of the implant and a lateral peeled back portion.

Referring to FIG. 5, the second embodiment reflects a replication of the middle section of the first embodiment of FIG. 4 including ligature 144 tied around intact cylindrical portion 146. An advantage of the multiple whole cylindrical section 146 and the associated ligatures 144, 150, 151 and 152 of the FIG. 5 embodiment of the invention is that the length of the operable implant, i.e. the inflated bleb portion may be increased as required by removing a ligature or plurality of ligatures section-by-section in series by simply removing the ligatures in a manner well-known tone skilled in the art, in this case an ophthalmologist. The present invention offers a post-surgical ability to customize the total surface area of the implant by increasing the functional surface area without the need of further surgery or an additional implant by simply removing a ligature 44 or a series of ligatures 144, 150, 151 and/or 152 from the whole cylinder portion(s) 146 after post-surgical intraocular pressure has been determined. It can readily be seen by one skilled in the art that the tube may contain any reasonable number of peeled back portions 138 and resulting open sides 140.

Figure 8:
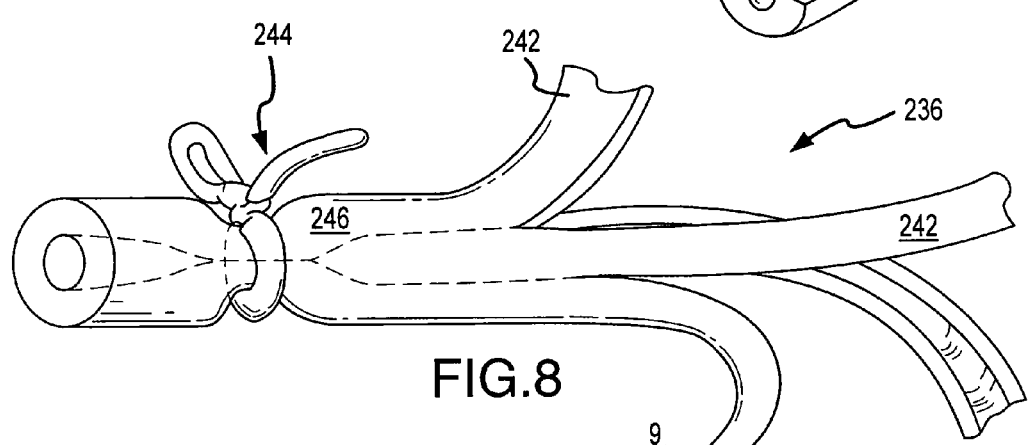
FIG. 8 is a schematic representation of a quadricated implant.
Figure 9:
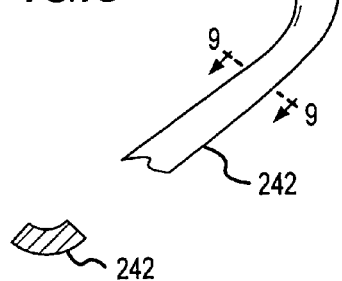
FIG. 9 is a cross section of a quadricated, C-shaped strand of the FIG. 8 implant taken along lines 9—9 of FIG. 8.

FIG. 8 shows a third embodiment of the invention similar in all respects to the first and second embodiments except the distal end 236 in quadricated, i.e. split into four sections 242 rather than two sections 32a. It can readily be seen by one skilled in the art that the distal end may be split into any reasonable number of sections. The purpose of forming the split end sections 32a, 242 and the peeled back lateral portions 38 is to allow a greater surface area but minimal total length of bleb. It does not matter that the nidi formed by the split ends become increasingly smaller in cross section. As the number of splits increase, the diameter of the bleb formed will be smaller in diameter and further reduced surface tension on the capsule, resulting in thinner capsule wall. The thickest part of the capsule forming around the C-shaped section 40, is only approximately three cell is thickness.

FIGS. 12–14 show a fourth embodiment of the invention. This embodiment includes latex scalloped nidus 338 extending from either side of the open-sided, C-shaped section 340. Scalloped nidus 338 may be attached to main body 340 of the implant by any well-known means. A cross section of scalloped nidus 338 is shown in FIGS. 13 and 14. Bleb 328 is shown formed around nidus 338 in FIG. 13. Scalloped portion 338 includes central or hub portion 370 and tip portions 372. Scalloped portion 338 has a radius of 50 microns from the center to the outer tip of the scallop, a tip width of 5 microns, and preferably extends up to 20 millimeters in a normal direction from the tube depending upon the requirements determined by the attending ophthalmologist.

The advantage of the scalloped geometry is that, if the capsule or bleb is deposited onto a smooth, solid surface, pressure from the anterior chamber may not always be sufficient to separate the capsule from the smooth, solid surface and inflate a volume in the subconjunctival space. If a bleb does not form or if the capsule remains attached to the implant material, it will not vent fluid and will not become functional. The number of scallops is a matter of choice, however 3, 4, 5, or 6 scallops is a reasonable number. Likewise, other forms providing a wave-like perimeter, such that the length of the perimeter is greater than the diameter of the form multiplied by pi, are within the scope of the present invention.

The method of the present invention for reducing intraocular pressure by creating a cylindrical bleb for producing improved accessory filtration comprises the steps of implanting a cylindrical tube having a proximal end and distal end, the distal portion of the cylindrical tube side wall being removed, into an eye to serve as a nidus for a conduit of aqueous humor to bypass angle structures consists of the steps of implanting the distal portion of the cylindrical tube under the conjunctiva, anchoring the proximal end of the cylindrical tube to the limbus, inserting the proximal, intact end of the tube into the anterior chamber through a needle track, ligating the distal end to prevent hypotony, allowing approximately one week for a bleb to grow around the tube, releasing a ligature around the proximal end after approximately one week to inflate the bleb, measuring the intraocular pressure to determine if additional drainage is required, if additional drainage is required, releasing additional ligatures whereby additional blebs are inflated.

Those with skill in the art of surgical treatment of glaucoma will readily see the invention's simplicity and flexibility. Thus the reader will see that the implant and method of reducing intraocular pressure of the present invention provides a more effective and customizable, yet economical solution for reduction of intraocular pressure.

While the above description contains many specificities, these should not be construed as limitations of the scope of the invention, but rather as an exemplification of preferred embodiments thereof. Many other variations are possible. For example, the material of the insert may be made of many types of elastomers other than latex; the size of the needle may be other than 23 gauge; the size, number, shape and dimensions of nidi and slip knot ligatures may vary and is not limited to four or to a "C" shape; the open diameter of the implant could vary; and the shape of the implant could be other than circular in cross section. The term "slip knot" as used here and in the claims includes any releasable knot. Accordingly, the scope of the invention should be determined not by the embodiments illustrated, but by the appended claims and their legal equivalents.

I claim:

1. A tube for implantation into the eye for replacement conduction of aqueous humor from the chambers of the eyeball to the subconjunctival tissue and ultimately the venous system, comprising:
    an elongated fluid conducting conduit having distal and proximate ends, a sidewall and an interior passageway and at least one longitudinally extending opening in the sidewall that exposes the interior passageway; and
    at least one nidi-forming means carried by the conduit and extending laterally therefrom to implement the formation of at least one aqueous filtration bleb in the tissue of the eyeball.

2. The tube of claim 1 and further comprising at least one releasable ligature circumscribing the conduit.

3. The tube implant of claim 2 where a releasable ligature is disposed intermediate the longitudinal sidewall openings.

4. The tube of claim 1 and further comprising anchoring means appended to the conduit to prevent the conduit from migrating from its placement site.

5. The tube of claim 4, wherein the anchor means comprises a plurality of conduit furcations.

6. The tube of claim 5 where the furcations are disposed at the distal end of the conduit.

7. The tube of claim 1 where the laterally extending nidi-forming means comprise partially detached longitudinal strips of the conduit having a free end and a fixed end, the later being attached to the conduit.

* * * * *